(12) United States Patent
D'Alerta (10) Patent No.: US 6,757,564 B2
(45) Date of Patent: Jun. 29, 2004

(54) MEDICAL SYSTEM USING BIOMOLECULAR TREATMENT

(76) Inventor: Mario D'Alerta, 11223 SW. 88 St. E101, Miami, FL (US) 33176

( * ) Notice: Subject to any disclaimer, the term of this patent is extended or adjusted under 35 U.S.C. 154(b) by 0 days.

(21) Appl. No.: 09/947,074

(22) Filed: Sep. 6, 2001

(65) Prior Publication Data

US 2003/0045915 A1 Mar. 6, 2003

(51) Int. Cl.$^7$ ................................................ A61N 1/08
(52) U.S. Cl. ........................................ 607/75; 607/46
(58) Field of Search ............................... 600/382, 384; 607/2, 39–41, 45, 46, 48, 50, 51, 72, 75, 43

(56) References Cited

U.S. PATENT DOCUMENTS

| | | | | |
|---|---|---|---|---|
| 4,607,639 A | * | 8/1986 | Tanagho et al. ......... | 128/419 E |
| 4,976,264 A | * | 12/1990 | Petrofsky ..................... | 607/48 |
| 5,417,719 A | * | 5/1995 | Hull et al. .................... | 607/46 |
| 5,421,817 A | * | 6/1995 | Liss et al. ..................... | 604/20 |
| 5,776,170 A | * | 7/1998 | MacDonald et al. ......... | 607/46 |
| 5,806,522 A | * | 9/1998 | Katims ........................ | 600/554 |
| 5,851,223 A | * | 12/1998 | Liss et al. ..................... | 607/46 |
| 6,432,986 B2 | * | 8/2002 | Levin .......................... | 514/330 |

* cited by examiner

Primary Examiner—Jeffrey R. Jastrzab
Assistant Examiner—Frances P. Oropeza
(74) Attorney, Agent, or Firm—Richard L. Huff (57) ABSTRACT

A method of scanning and treating areas of the human body with transcutaneous low intensity direct current. A device is used which comprises a source of low intensity direct current, means for controlling the parameters of the current, a cathode terminal, and an anode terminal. A scanning method is used to determine the proper amperage for the treating method. In the scanning method, the cathode and anode are applied to the skin of a patient and increasing strengths of current are applied. The strength of the current is noted when the patient is first aware of the current and when the patient is made uncomfortable by the current. These two values are averaged to determine the operating current. The treatment method is carried out by applying the anode to an activity point identified in the specification, applying the cathode to the area to be treated, and applying the operating current.

6 Claims, 5 Drawing Sheets

MEDICAL SYSTEM USING BIOMOLECULAR TREATMENT

BACKGROUND OF THE INVENTION

1. Field of the Invention

The field of this invention relates to the application of transcutaneous low intensity direct current (TLIDC) to specified points on the human body to bring about cell regeneration and relief of pain.

2. Description of the Related Art

It is known in the art to apply direct current to the skin of humans afflicted with a variety of conditions to bring about relief. Thus, Fragnet in U.S. Pat. No. 4,226,246 discloses a method for maintaining the negative potential of human cells which comprises applying a direct current to the skin for cycles of 4 minutes on and 2 minutes off. No particular location on the body is recommended. U.S. Pat. No. 6,016,451 issued to Sanchez-Rodarte discloses holding spaced-apart electrodes carrying direct current over the skin of a patient in order to regulate the nervous system. The device of this invention is to be worn by the patient in any of a number of named areas of the body. No specific locations of use are identified. Greenspan, et al., in U.S. Pat. No. 6,108,580, disclose a method of stress reduction which comprises applying direct current in alternating positive and negative polarities to the skin. The current is applied to the skin for a matter of minutes and no specific location is taught as being better than another. Applicant's prior patent, U.S. Pat. No. 5,423,874, discloses a patch to be applied to the skin, which patch contains an electrical current supplying direct current to an anode and a cathode. The patch is useful for relieving pain. No particular area of the body is recognized as being particularly useful. While the application of direct current to the skin has been widely taught for a variety of conditions, there is no recognition of the most effective areas of application.

SUMMARY OF THE INVENTION

The method of the present invention employs the application of direct current to the skin of a patient to treat a number of conditions. The method employs a TLIDC which produces a negative ion output to treat these conditions. The method may be used in a home or hospital setting. Specific areas of application are taught which greatly enhance the efficacy of the treatment.

DESCRIPTION OF THE PREFERRED EMBODIMENTS

Our earth is divided into three component elements; North, Equator, and South. The North pole is negative, the equator is neutral, and the South pole is positive. There is a physical law which states that the upper part of everything on our planet is negative, its midpoint is neutral, and its lower part is positive. Regardless of how many times something (e.g., the Earth) is divided, the polarities will always maintain the same orientation. This follows to the atomic level.

Atoms comprise three fundamental particle types: protons (particles with a positive-charged mass), neutrons (particles having the same mass as protons but containing no electrical charge), and electrons (particles having a much smaller mass than protons but containing a negative electrical charge). The atom particles are arranged as a tiny solar system. The protons and neutrons stay united by a great cohesive force and they form the central nucleus of the atom. The nucleus, which is very dense, corresponds to the sun in our solar system. The electrons rotate at a great speed around the nucleus, orbiting like the planets around the sun. The atom stays stable due to the attraction force exercised on the positively charged nucleus and the orbital distribution follows a defined pattern similar to the North and South poles and our gravity.

Molecules are the smallest portion of any substance, element, or compound that is self-sufficient. All molecules are made up of atoms.

A study of the living universe reveals an immense diversity of forms. There are around four million species of bacteria, protozoa, vegetable zoans, and animals with different morphology, function, and behavior. A common thread exists in that all of these species contain cells having molecular ions. All cells exist of the same elements as those in the surrounding world.

All living cells contain plasma, which comprises organic substances such as glucose, lipids, and nitrogenated substances. The plasma is surrounded by very thin membranes which regulate the entrance and exiting of food and wastes which are made up of proteins, carbohydrates, fatty substances, and inorganic ions like sodium and chloride.

Figure 1:
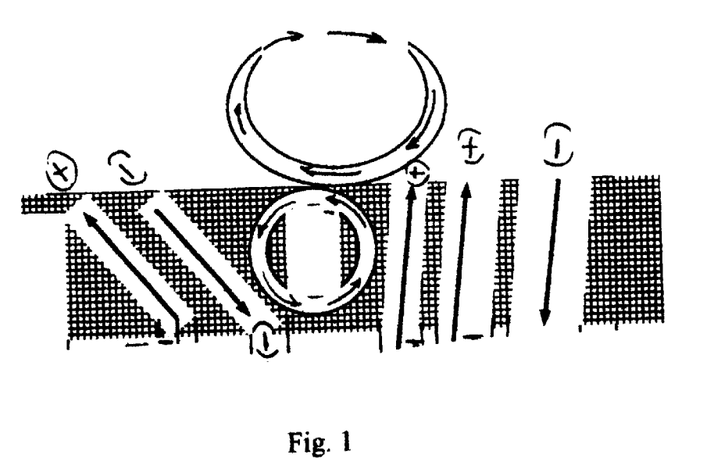
FIG. 1 illustrates a typical cell membrane showing ion transport across the membrane.

The cell membranes are made up of lipids and proteins. As shown in FIG. 1 these membranes are perforated with small holes through which substances, such as oxygen, can enter into the cytoplasm and the waste products, such as carbonic anhydride, can exit. Molecules whose sizes are too big to pass through the membranes are dissolved in its lipids and transported in the dissolved form to the interior of the cell.

Other nutrients, such as glucose, fatty acids, and amino acids that form the proteins pass into the interior of the cells because of the presence of some well-known chemical substances known as membrane transporters.

Atoms make up the cell, and atoms, in turn, are made of electrically charged ions having weight and polarity. Since polarities possess certain situational characteristics at their poles, cells are capable of discriminating among molecules, admitting some and not admitting others.

The cytoplasm lies within the cell membrane. The cytoplasm is a watery substance which makes up most of the cellular mass and supplies the matrix in which the chemical changes take place. A complex system of interconnected tunnels lies within the cytoplasm. Several hundred mitochondria exist in the cytoplasm of each cell. The mitochondria extract energy from the nutritious substances. This energy is used to carry out chemical, mechanical, and electrical work. Inhaled oxygen is necessary to metabolize the glucose and fatty acids. This metabolism proceeds through a series of steps resulting in the production of adenosinetriphosphate (ATP).

The cell in a human or other mammalian body can be compared to an atom in that it has three parts. In its center are the positively charged nucleus and neutral materials surrounded by negatively charged cytoplasm. It is well known that two poles of different polarities attract each other and two poles of the same polarity repel each other. Cells are capable of repelling like charges and attracting unlike charges just like other electric poles. It is for this reason that prior art methods of electrical therapies have not yielded desired results. The cells reject the like charges and the electric currents do not bring relief.

Figure 2:
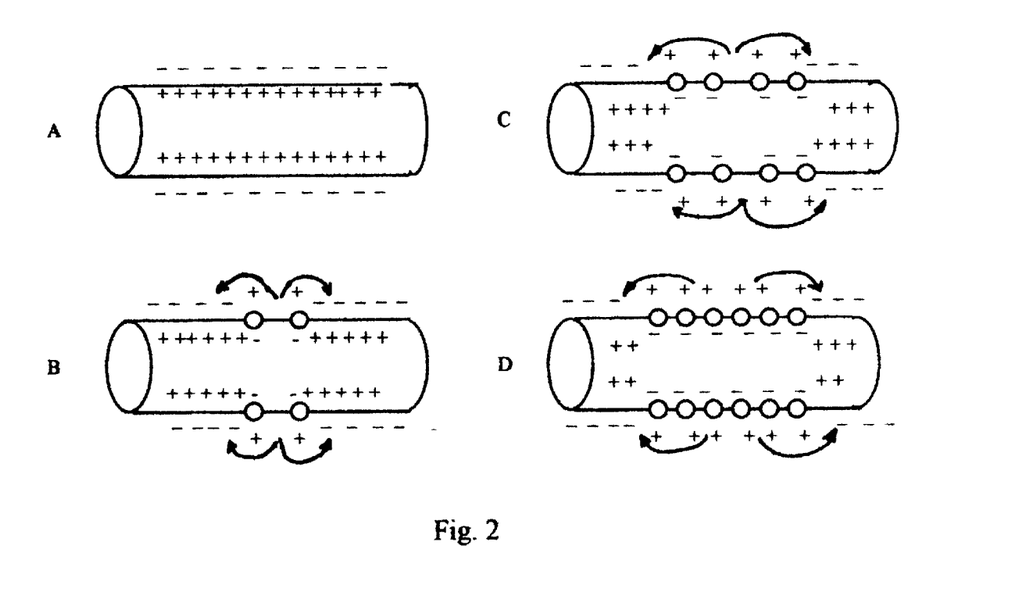
FIG. 2 illustrates the electrical charges exhibited in a cell undergoing progressive damage.

FIG. 2 shows the location of electrical charges during cellular decomposition. "A" depicts a cell in the healthy condition having a negative charge in the cytoplasm of the cell and a positive charge in the nucleus of the cell. "B" indicates a cell which has an ailment or lesion. As a consequence, the affected area contains a positive charge in the cytoplasm of the cell and a negative charge on the nucleus of the cell. The cells in "C" and "D" indicate a worsening of the condition and the corresponding change in the electrical charges on the cytoplasm and nucleus of the cell. When the method of the present invention is used, the cell resumes the condition displayed in "A".

Likewise, the human body is also divided into three parts; the head, trunk, and lower extremities.

The method of the present invention takes the above discussion into account and produces unexpectedly superior results compared to the prior art methods.

The method of the present invention involves scanning affected areas and applies painless electrical stimulation to the affected areas. TLIDC having a negative ion output is applied to select areas of the body to bring about desired results. The method of this invention can be used by the individual or in large medical settings. The method of this invention provides symptomatic relief management for chronic, long term, intractable pain. It serves as an adjunctive treatment in the management of post-surgical and post-traumatic acute pain. It is useful for the following conditions: general pain, arthritis, rheumatism, sciatica, lumbago, backache, neck pain, respiratory ailments, torticollis, hemiplegia, quadriplegia, abscess, anemia, goiter, cramps, small varices, post-operative scarring, cellulitis, fatigue, impotence, frigidity, acne, corns, hemorrhoids, incontinence, bone fractures and implants to effect biological bone tissue regeneration, and decubitus ulcer. The method of this invention also reestablishes sound sleep and works as an antibacterial agent, improves immunity, and increases physical strength.

The devices used in the present invention are known in the prior art. The treatment devices have a source of direct current, means for controlling the parameters of the current, and two cables with contact terminals, one anode and one cathode.

The anode is the positive electrode. The tissues affected by this electrode exhibit an acidic reaction, increased protein density, increased pain, increased cell permeability, decreased vascular budding and cell proliferation, decreased blood flow, and increased thermal effect.

The cathode is the negative electrode. The tissues affected by this electrode exhibit an alkaline reaction, decreased density of protein, decreased pain, bactericidal activity, increased cell permeability, increased blood flow, and decreased thermal effect.

The anode is affixed to the patient's body and is immobilized with an elastic band. The cathode is the negative terminal and is designed to be in motion during the treatment and scanning process. Preferably, the cathode has a handle for proper handling.

The method of this invention makes possible a highly accurate electrical treatment of a wide variety of surface areas, nerves, muscles, and organs of the mammalian body. This is due to the determination of the forty-six activity points shown in FIGS. 5–9.

The method of this invention involves scanning and treatment. The scanning provides the information for adjusting the parameters of the treatment steps. The results of the scanning and treatment steps can be readily recorded in the patient's clinical history.

In carrying out the scanning step of the method of this invention, the anode is placed at a prudent distance from the affected area. The cathode is applied smoothly on the patient at the affected area a few inches from the anode. Once both the anode and the cathode have been placed on the patient, the electrical output of the device is increased until the patient perceives a first sensation of an electronic pulse. For the clinical history, the number that appears in the graduated scale of the stimulator setting will be written. This will be the minimum level for the patient that day. The electrical output is increased until the patient perceives that the sensation is uncomfortable. The number on the graduated scale corresponding to this sensation is noted for the history and is the maximum level for the patient that day. The scanning time of activity points should not exceed four seconds.

At the beginning of the course of treatment, at least ten activity points should be scanned before treating the affected area. In the beginning of the treatment process, the treatment area will be an activity point associated with the affected area. As the treatment process progresses, the number of activity points scanned may be decreased. Eventually, in the treatment of skin conditions, treatment will be applied to the affected area directly rather than an activity point.

In a sick body, any mechanical or electrical intrusion or anything that comes close and stimulates the problem areas will only serve to further irritate the patient. Therefore, when treating a skin condition, the scanning step is performed as follows. The first time the electro-mechanical device is used, the cathode is placed in the center of the damaged area and is moved outward relative to the extent of the injured area. This enables the patient to lose the defensive mechanism of rejecting treatment as well as the sense of distance between activity points, allowing treatment to filter in and purify from one activity point to the other until it gets to the affected areas. The ion impulses will arrive perfectly pure and sufficiently strong to produce a quick cellular regeneration with a regenerative potential quality up to three times stronger than the patient's own.

With respect to the setting of the frequency of the electric ion pulses in the method of this invention, the frequency should not exceed the patient's own electric pulse. One of the reasons why many electric treatments do not work is because the patient rejects any other sensation caused by the treatment in addition to the pain already present. This is another reason why the scanning should be done at a distance from the affected area.

The treatment steps of the method of this invention are performed as follows. Halfway between the minimum and maximum levels as determined above is the treatment level for the patient for that day. The power output at the treatment level produces a sensation which is noticed by the patient at once. The above treatment method is repeated daily for the course of the entire treatment. As the course of treatment progresses, the patient will tolerate a greater power output. If the patient is being treated for a painful condition, it will be noticed that the pain will diminish until it disappears and that the pain will disappear for longer periods of time.

When a nerve fiber is at rest, there is a power difference between the external and internal surface of the plasmatic membrane. The external surface has a positive charge and the internal surface has a negative charge. In this state, the plasmatic membrane is not permeable to sodium ions, which are found in the external surface. Accordingly, there is a patterned distribution of other ions on the outside and inside of this surface. If the power difference throughout the membrane decreases below a certain level, the membrane becomes permeable for the sodium ions.

If a negative electric impulse is induced according to the method of this invention, it stimulates the nerves and the sodium ions begin to penetrate the axon causing a bigger decrease in the power difference and a permeability increase of the membrane to other ions. With continued stimulation, there is an inversion in power difference. The external surface of the membrane becomes negatively charged and the internal surface positively charged. This is the desired condition of a healthy cell and its ions.

When an electrical stimulus is applied to a motor nerve trunk, the impulses pass to all the muscles that are supplied by the nerve trunk beyond the stimulation point, provoking a muscular contraction. When the current is applied directly to an innervated muscle, the nervous fibers in the muscle are stimulated in the same way; the maximum response being obtained by stimulating the points located where the main nerve penetrates the muscle. In the case of deep muscles, it is at the point where the muscle emerges from under the cover which wraps the top muscles.

When a muscle contracts because of electric stimulation, the changes that take place in the muscle are similar to those that take place due to voluntary natural contractions.

Electric stimulation results in a 50% increase in strength as well as improved resistance to fatigue, creating chemical fuel. It reactivates and boosts the ATP cycle. In comparison, the contractions because of exercise, work, or sport, where the muscle gets tired and has to have a resting period for greater strength, the increase in strength is only about 10%.

In a correct electrical stimulation of the nervous system supplying the motor neurons, a treatment according to the method of this invention lasts approximately 30 minutes and provides a superior benefit in comparison to the exercise of running. Using the method of the invention, there is an additional benefit in that there is no fatigue. Thus, the method of the invention, when used to stimulate muscles, finds use in treating paralyzed patients, use in treating the elderly or others who are incapable of strenuous exercise, and use in maintaining muscle tone on those who are not subject to earth's gravitational forces.

Figure 3:
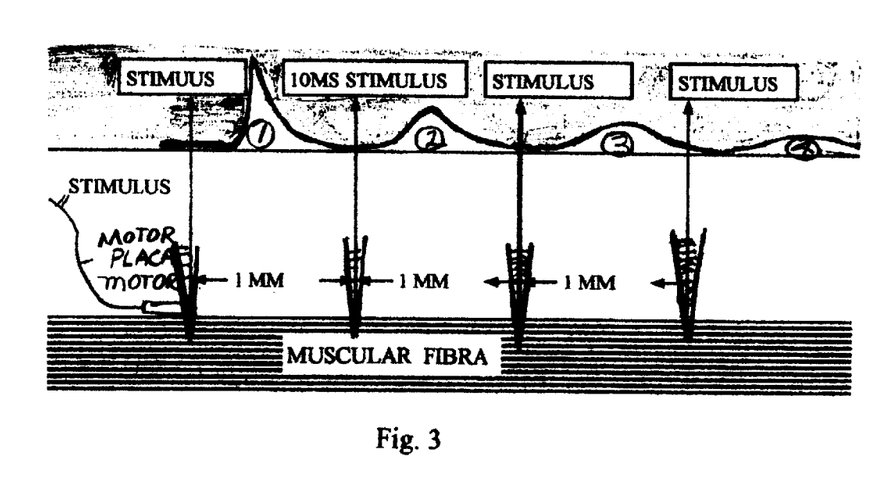
FIG. 3 illustrates electrical amplitude behavior in a muscle subject to electrical stimulation.

Referring to FIG. 3, the amplitude behavior of an electrical stimulus on a muscle fiber is depicted. The Fig. depicts the amplitude of an electrical charge up to 4 mm from the source and also depicts the amplitude at 1 mm intervals traveling at 1 mm per second. During the first stimulus, there is a strong, wide spectrum. In the second stimulus, the effect is 50% less than the first. In the third stimulus, the effect is 50% less than the second, and in the fourth stimulus, the effect is 50% less than the third. Thus, as the stimulus travels, its strength declines. However, when the effect of the stimulus is about 4 mm away from the source of the stimulus, it is amplified and it travels throughout the body until it has the desired effect of changing the polarity and permeability of the targeted cells.

According to the method of the present invention, the stimulus is applied to key activity points as shown in FIGS. 5–9. The impulses from the stimulus travel through nerve fibers at a speed of 10 mm/sec. If the pulses are sustained every 2 to 4 seconds on the recommended activity points, the scanning and treatment steps of this invention become highly efficient.

The treatment method is concluded by performing a 4-second application on the affected area.

Figure 4:
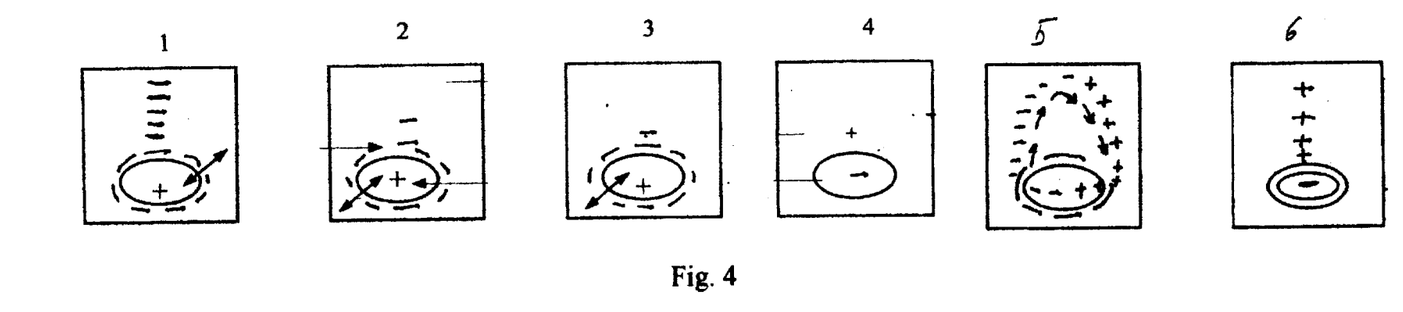
FIG. 4 illustrates the permeability changes associated with electrical changes during normal sleep and wake periods.
Figure 5:
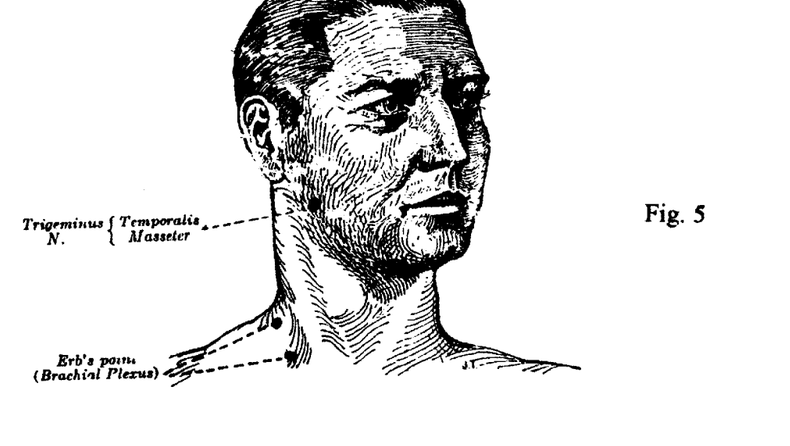
FIG. 5 illustrates the activity points in the brachial plexus which are used in the method of this invention.

A graphic description of the normal cell in the wake/sleep cycle of a healthy individual cell is given in FIG. 4. The electrical charges and permeability status of the cell are shown in various circumstances. In step 1, the cell membrane is permeable as the cytoplasm is negatively charged and the positive charges are in the nucleus during the wake stage of a healthy individual. In step 2, negative charges continue to promote permeability, but the charge is declining. The patient having this cell would begin to fatigue. In step 3, the cell exhibits normal permeability, however the electrical charge is only 4 seconds away from the inversion of its natural and typical polarity occurring the restoring daily sleep for energy renewal. In step 4 the sleeping individual is at rest and in only 4 seconds the polarity was inverted. Step 4 shows that the negative charges are found in the nucleus and the cell membrane is impermeable. When the cell wall is permeable, the interior of the cell accumulates ATP, the negative electrons of which are used for energy production or recharging the cell's energy. This energy restoration process takes place when the cell is in an almost absolute impermeable state. Upon awakening, the individual is energized, as shown in steps 5 and 6. The permeability-to-impermeability state and the positive-to-negative cycle are shown in steps 5 and 6. This step is accomplished in only 4 seconds, then the cell returns to the high energy state shown in step 1.

The method of this invention makes possible a highly accurate electrical treatment of a wide variety of surface areas, nerves, muscles, and organs of the mammalian body. This is due to the determination of the forty-six activity points shown as round points in FIGS. 5–9.

In the head, the activity point is the trigeminus nerve in the temporalis masseter muscle.

In the neck, the activity points are Erb's point and the brachial plexis.

In the shoulder, the activity points are the circumflex nerve in the anterior and middle portions of the deltoid muscle.

In the arm, an activity point is located over the biceps muscle. Other activity points are the median nerve in the pronator teres, flexor carpi radialis, and flexor sublimes digitorum muscles. Another activity point is the ulnar nerve in the flexor carpi ulnaris muscle. Other activity points are over the palmaris longus and flexor profindus digitorum muscles.

In the wrist, activity points are the median nerve in the flexor longus pollicus and opponens pollicus muscles.

In the hand, activity points are the median and ulnar nerves in the four lumbricales muscles.

In the anterior of the lower limb, activity points are the femoral nerve in the groin, the femoral nerve in the vastus internus muscle, over the vastus externus muscle, over the center of the peroneus longus muscle, over the extensor digitorum brevis muscle and the deep peroneal nerves in the four interossei muscles.

In the posterior of the lower limb, activity points are over the gluteus maximus muscle and the tibial nerve at the level of the knee.

To affect changes in the visceral organs, activity points located in the spinal column at the level of T-2 to T-5, L-1, and L-2 are useful. Additional activity points are at the level of S-1 and S-2 near the center of the half of the body to be treated.

Figure 6:
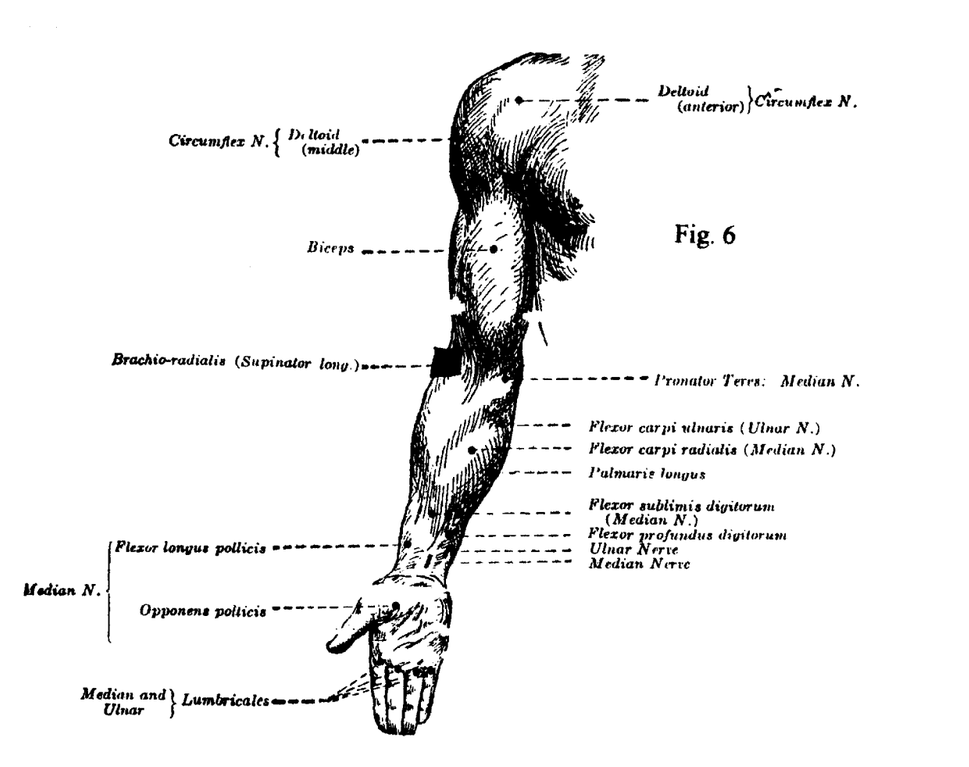
FIG. 6 illustrates the activity points of the anterior aspect of the upper extremity which are used in the method of this invention.
Figure 7:
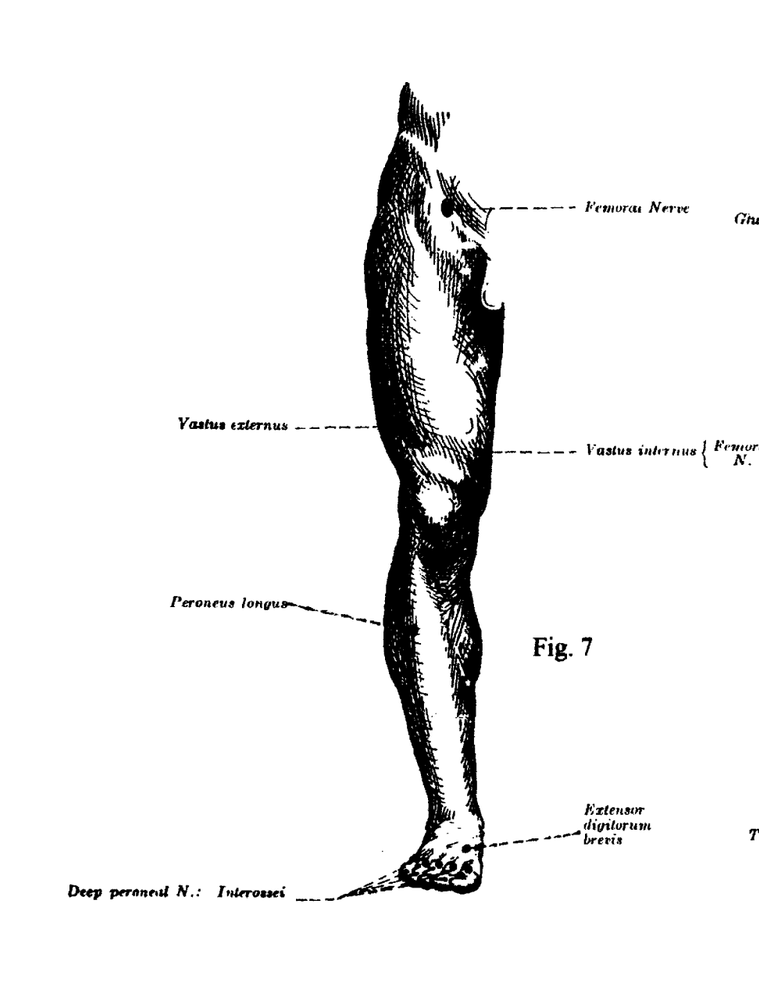
FIG. 7 illustrates the activity points of the anterior aspect of the lower extremity which are used in the method of this invention.
Figure 8:
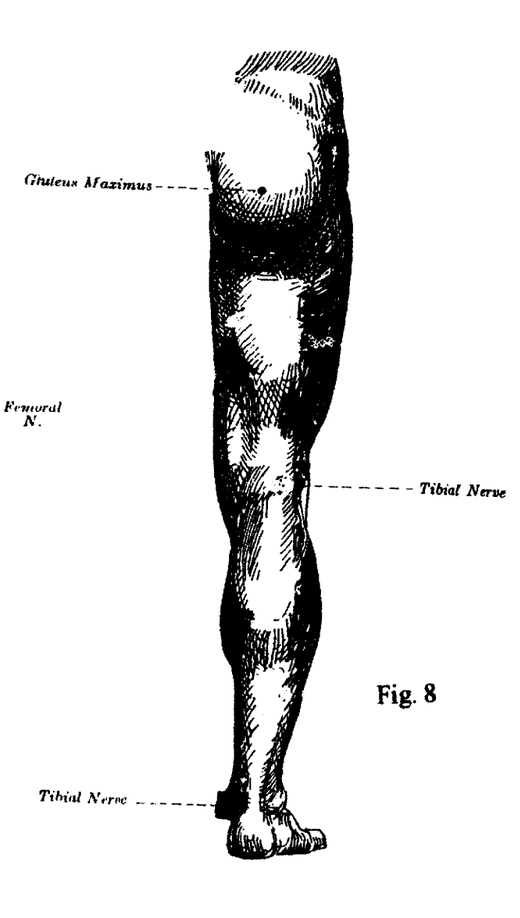
FIG. 8 illustrates the activity points of the posterior aspect of the lower extremity which are used in the method of this invention.
Figure 9:
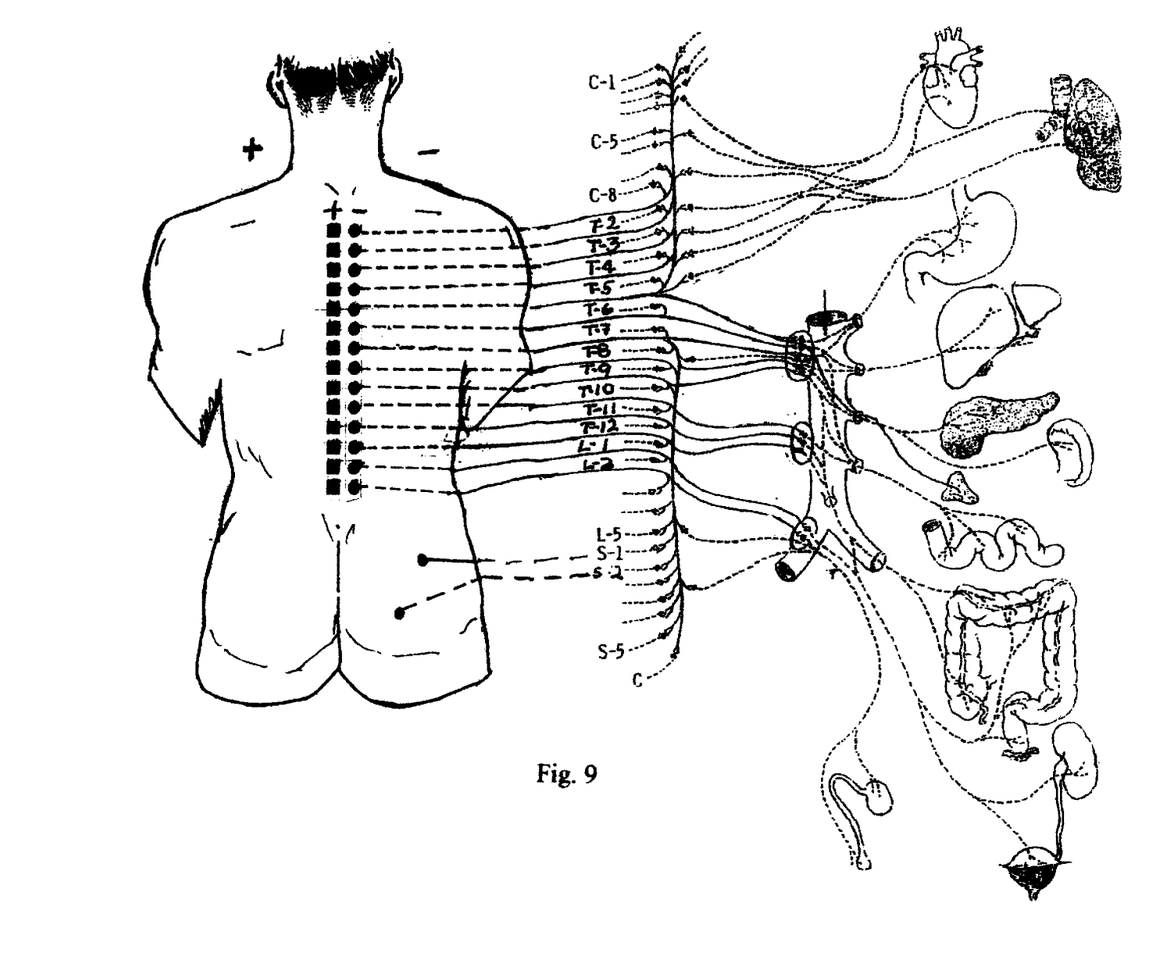
FIG. 9 illustrates the activity points of the posterior aspect of the trunk which are used in the method of this invention.

In FIGS. 6, 8, and 9, in addition to the activity points, indicated by round points, there are square marks. In practicing the method of the present invention it is desirable for the anode to be placed on the square marks and the cathode to be placed on the round points. Thus, in stimulating an internal organ shown in FIG. 9, the anode should be placed on the square marks corresponding to T-2, T-3, T-4, and T-5 and for points corresponding to S-1 and S-2 while the cathode should be placed on the corresponding round points and the specified current is applied to each spot for the specified time. The cathode should be applied to the side of the body which is to be treated and the anode should be applied to the opposite side of the spinal column at the corresponding level.

The current parameters used in the method of the present invention are a direct (galvanic) current having a unidirectional constant flow and being of low current, an amperage of about 1 mA, a frequency of 0.3–1000 Hz, and a pulse width of 10–1000 μSec. Lower frequencies are used in acute conditions whereas higher frequencies are used in chronic conditions A single treatment of approximately 30 minutes is given daily.

A minimum amount of time is necessary for the electric current to produce nerve or muscle stimulation. This time is expressed by the chronaxie, which is the time necessary for a current which is twice the rheobase to produce a response. The rheobase is the minimum amount of current necessary to stimulate a nerve or muscle.

Although the invention has been described in detail, it is to be clearly understood that the same is by way of illustration and example, and is not to be taken by way of limitation. The spirit and scope of the present invention are to be limited only by the terms of the appended claims.

I claim:

1. A method of bringing about cell proliferation or pain relief in a patient in need of cell proliferation or pain relief, which comprises:
    (a) providing an electrical apparatus comprising a source of direct current having amperage, frequency, and pulse width parameters, means for controlling the parameters of the direct current, a cable having a cathode terminal, and a cable having an anode terminal;
    (b) placing the anode terminal on the skin of the patient in an area selected from the group consisting of:
        i) the brachio-radialis nerve over the supinator longus muscle and
        ii) the tibial nerve in the ankle,
    c) placing the cathode terminal on an activity point of the skin of the patient, which activity point is on the side of the patient to be treated and is selected from the group consisting of:
        i) the circumflex nerve in the anterior of the deltoid muscle, the circumflex nerve in the middle of the deltoid muscle, over the biceps muscle, the median nerve in the pronator teres muscle, the median nerve in the flexor carpi radialis muscle, the median nerve in the flexor sublimes digitorum muscles, the median nerve in the flexor longus pollicis muscle, the median nerve in the opponens pollicis muscle, the ulnar nerve in the flexor carpi ulnaris muscle, over the palmaris longus muscle, over the flexor profundus digitorum muscle, or over the median and ulnar nerves in the lumbricales muscles and
        ii) over the femoral nerve in the groin, over the femoral nerve in the vastus externus muscle, over the femoral nerve in the vastus internus muscle, over the pronatus longus muscle, over the exterior digitorum brevis muscle, over the deep peroneal nerve in the interossei muscles, over the gluteus maximus muscle, or over the tibial nerve in the knee;
    wherein each of the Roman numerals in (c) corresponds with a like Roman numeral set forth in (b); and
    (d) performing a treating step by operating the electrical apparatus to supply the direct current.

2. The method of claim 1, wherein the direct current has an amperage of about 1 mA, a frequency of about 0.3–1000 Hz, and a pulse width of 10–1,000 μSec.

3. The method of claim 2, wherein the treating step lasts approximately 30 minutes.

4. A method of scanning and treating an area of the skin of a patient in need of cell proliferation or pain relief, which comprises:
    (A) scanning an area following the steps comprising:
        (i) providing an electrical apparatus comprising a source of direct current having amperage, frequency, and pulse width parameters, means for controlling the parameters of the current, a cable having a cathode terminal, and a cable having an anode terminal,
        (ii) placing the anode terminal on the area of the skin to be scanned,
        (iii) placing the cathode terminal on the area of the skin to be scanned,
        (iv) operating the electrical apparatus to supply the direct current,
        (v) determining a minimum amperage value of the direct current for the patient by increasing the amperage of the direct current until the patient is aware of the direct current and recording the thus-determined amperage value as the minimum value,
        (vi) determining a maximum amperage value of the direct current for the patient by further increasing the amperage of the direct current until the patient indicates the presence of an uncomfortable sensation due to the direct current and recording the thus determined current amperage value as the maximum value, and
        (vii) averaging the minimum and maximum values to determine an operating value, and
    (B) treating the area following the steps comprising;
        (a) placing the anode terminal on the skin of the patient to be treated, which area is selected from the group consisting of:

i) the brachio-radialis nerve over the supinator longus muscle and
ii) the tibial nerve in the ankle;
(b) placing the cathode terminal on an activity point on the skin of the patient to be treated, which activity point is on the side of the patient to be treated and is selected from the group consisting of:
i) the circumflex nerve in the anterior of the deltoid muscles the circumflex nerve in the middle of the deltoid muscle, over the biceps muscle, the median nerve in the pronator teres muscle, the median nerve in the flexor carpi radialis muscle, the median nerve in the flexor sublimes digitorum muscles, the median nerve in the flexor longus pollicis muscle, the median nerve in the opponens pollicis muscle, the ulnar nerve in the flexor carpi ulnaris muscle, over the palmaris longus, muscle, over the flexor profundus digitorum muscle, or over the median and ulnar nerves in the lumibricales muscles,
ii) over the femoral nerve in the groin, over the femoral nerve in the vastus externus muscle, over the femoral nerve in the vastus internus muscle, over the pronatus; longus muscle, over the exterior digitorum brevis muscle, over the deep peroneal nerve in the interossei muscles, over the gluteus maximus muscle, or over the tibial nerve in the knee; wherein each of the Roman numerals in (b) corresponds with a like Roman numeral set forth in (a); and
(c) performing a treating step by operating the electrical apparatus to supply the direct current.

5. The method of claim 4, wherein the direct current has the amperage of about 1 mA, the frequency of about 0.3–1000 Hz, and the pulse width of 10–1,000 $\mu$Sec.

6. The method of claim 5, wherein the treating step is given for approximately 30 minutes.

* * * * *